US008182768B2

(12) United States Patent
Tipler et al.

(10) Patent No.: US 8,182,768 B2
(45) Date of Patent: May 22, 2012

(54) INTERFACE ASSEMBLY FOR PRE-CONCENTRATING ANALYTES IN CHROMATOGRAPHY

(75) Inventors: Andrew Tipler, Trumbull, CT (US); John H. Vanderhoef, Stratford, CT (US); James E. Botelho, Danbury, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 2119 days.

(21) Appl. No.: 11/251,187

(22) Filed: Oct. 14, 2005

(65) Prior Publication Data

US 2006/0099716 A1    May 11, 2006

Related U.S. Application Data

(63) Continuation of application No. PCT/US2004/011434, filed on Apr. 14, 2004.

(60) Provisional application No. 60/462,731, filed on Apr. 14, 2003, provisional application No. 60/481,626, filed on Nov. 12, 2003.

(51) Int. Cl.
*G01N 30/02* (2006.01)

(52) U.S. Cl. .......... 422/531; 422/89; 422/501; 422/513; 422/534; 436/174; 436/177; 436/178; 436/180; 73/23.41; 73/23.42; 95/88; 95/116; 95/141; 96/105; 96/106

(58) Field of Classification Search ........ 95/88; 96/105, 96/106; 73/23.41, 23.42; 422/89.101, 88, 422/89, 501, 513, 531, 534, 535
See application file for complete search history.

(56) References Cited

U.S. PATENT DOCUMENTS

| 4,003,257 A | 1/1977 | Fletcher et al. ................ 73/23.1 |
| 4,096,734 A | 6/1978 | Khayat .......................... 73/23.1 |
| 4,351,802 A | 9/1982 | Baylis et al. .................... 422/89 |
| 4,484,483 A | 11/1984 | Riegger et al. ............ 73/864.23 |

(Continued)

FOREIGN PATENT DOCUMENTS

| JP | 9133668 A | 5/1997 |
| WO | 9817998 A1 | 4/1998 |

OTHER PUBLICATIONS

Mark A. Klemp et al: "Cryofocusing Inlet with Reverse Flow Sample Collection for Gas Chromatography" (Analytical Chemistry, American Chemical Society. Columbus, U.S., vol. 65, No. 18, Sep. 15, 1993, 6 pages).

(Continued)

*Primary Examiner* — Jill Warden
*Assistant Examiner* — Shogo Sasaki
(74) *Attorney, Agent, or Firm* — St. Onge Steward Johnston & Reens LLC

(57) ABSTRACT

A system for interfacing a sampling device and a chromatograph and for pre-concentrating analytes in a sample prior to introducing the sample into the chromatographic column is generally disclosed comprising an interface housing with a first channel and an adsorbent housing with a second channel, which contains at least one adsorbent. Valveless conduits permit fluid to be communicated between the sampling device and the first channel, between the first channel and the second channel, and the first channel and the column. In some embodiments, fluid flows in one direction when the analytes are adsorbed and in the opposite direction when analytes are desorbed. In certain embodiments, two different adsorbents are disposed in the second channel to adsorb different types of analytes.

16 Claims, 6 Drawing Sheets

U.S. PATENT DOCUMENTS

| | | | |
|---|---|---|---|
| 5,441,700 A | 8/1995 | Markelov | 422/83 |
| 5,545,252 A | 8/1996 | Hinshaw et al. | 95/15 |
| 5,711,786 A | 1/1998 | Hinshaw | 95/82 |
| 5,720,798 A | 2/1998 | Nickerson et al. | 96/102 |
| 5,792,423 A | 8/1998 | Markelov | 422/83 |
| 5,827,945 A * | 10/1998 | Arnold | 73/23.42 |
| 5,872,306 A | 2/1999 | Arnold | 73/23.37 |
| 5,932,482 A | 8/1999 | Markelov | 436/181 |
| 6,365,107 B1 | 4/2002 | Markelov et al. | 422/83 |
| 6,395,229 B1 | 5/2002 | Markelov | 422/83 |
| 6,395,560 B1 | 5/2002 | Markelov | 436/181 |
| 6,652,625 B1 | 11/2003 | Tipler et al. | 95/82 |

OTHER PUBLICATIONS

Juan M, Sanchez et al: "On-Line Multibed Sorption Trap and Injector for the GC Analysis of Organic Vapors in Large-Volume Air Samples" (Analytical Chemistry, American Chemical Society. Columbus, U.S., vol. 75, No. 4, Feb. 15, 2003, 8 pages).

Chia-Jung Lu et al: "A Dual-Adsorbent Preconcentrator for a Portable Indoor-VOC Microsensor System" (Analytical Chemistry, American Chemical Society. Columbus, U.S., vol. 73, No. 14, Jul. 15, 2001, 9 pages).

European Search Report, Sep. 20, 2007, 9 pages.

* cited by examiner

INTERFACE ASSEMBLY FOR PRE-CONCENTRATING ANALYTES IN CHROMATOGRAPHY

This application is a continuation of International Patent Application No. PCT/US2004/011434 filed on Apr. 14, 2004, which designates the United States and claims priority of U.S. Provisional Patent Application Nos. 60/462,731 filed on Apr. 14, 2003 and 60/481,626 filed on Nov. 12, 2003.

FIELD OF THE INVENTION

The present invention relates to a system for interfacing devices in chromatography. More specifically, the invention relates to a system for interfacing a sampling device and a chromatograph that preconcentrates the analytes to be measured.

BACKGROUND OF THE INVENTION

Chromatography is essentially a physical method of separation in which constituents of a test sample in a carrier gas or liquid are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various elements of the sample—which differ based upon differences among distribution coefficients of the elements—cause the sample to be separated into the respective elements. At the end of the column, the individual components are more or less separated in time. Detection of the gas provides a time-scaled pattern, typically called a chromatogram that by calibration or comparison with known samples, indicates the constituents of the test sample. An example of the process by which this occurs is described in U.S. Pat. No. 5,545,252 to Hinshaw.

Often, the sample is first obtained using a sampling device, which subsequently transfers the sample to the chromatograph. One means of obtaining a sample and introducing it into a chromatographic column is known as "headspace sampling." In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time. An example of such a sampling device is disclosed in U.S. Pat. No. 4,484,483 to Riegger et. al. An example of a chromatographic system employing such a sampling device is disclosed in U.S. Pat. No. 5,711,786 to Hinshaw, which describes using a chromatographic injector between the vial and the chromatographic column.

Typically, it is desired to pre-concentrate the analytes in the sample, and occasionally, remove moisture therefrom, prior to introducing the sample into the chromatographic column. Accordingly, as disclosed in U.S. Pat. Nos. 5,792,423 and 6,395,560 to Markelov, these systems will typically include some kind of "trap" for this purpose, which retains the analytes as they are carried through the trap, and which are later released from the trap, usually by heating, and swept into the chromatographic column.

Various types of traps have been suggested to perform this pre-concentration (and possible moisture removal) prior to introducing the sample into a chromatographic column. Often, it is advantageous to use an adsorbent trap of some sort to adsorb the analytes, which can later be desorbed, as opposed to an absorbent because, since the anhydrous substance absorbs water, repeated use of the anhydrous substance is likely to be limited and require frequent replacement. Accordingly, numerous arrangements employing an adsorbent trap have been employed for the purpose of pre-concentrating the analytes of a sample extracted by a sampling device such as a headspace sampler. Examples of such arrangements are disclosed in U.S. Pat. No. 5,932,482 to Markelov and U.S. Pat. No. 6,652,625 to Tipler.

However, to date, these systems have resulted in a number of disadvantages. First, in order to accomplish this multiple stage process of extracting a sample fluid, transferring it to the trap, trapping it and untrapping it, and transferring it to the chromatographic column, these systems have employed complex assemblies of parts and/or valves situated in the flow path of the fluid containing the analytes to be measured. These extra devices and valves not only increase cost and space, but increase dead-volume areas and surface active sites. This results in sample dispersion, dilution, or loss, and causes excessive peak broadening on the chromatogram. Another disadvantage present in some of these systems is the unidirectional path of flow for both adsorption and desorption, inhibiting the ability to first trap heavier compounds and then more volatile compounds by using multiple adsorbents.

What is desired, therefore, is a system for interfacing a sampling device and a chromatograph and for pre-concentrating analytes in a sample prior to introducing the sample into the chromatographic column that is inexpensive to manufacture and does not take up a lot of space. What is further desired is a system for interfacing a sampling device and a chromatograph and for pre-concentrating analytes in a sample prior to introducing the sample into the chromatographic column that reduces the amount of dead volume areas and surface active sites. What is also desired is a system for interfacing a sampling device and a chromatograph and for pre-concentrating analytes in a sample prior to introducing the sample into the chromatographic column that facilitates the use of multiple adsorbents.

SUMMARY OF THE INVENTION

Accordingly, an object of the present invention is to provide a system for interfacing a sampling device and a chromatograph and for pre-concentrating analytes in a sample prior to introducing the sample into the chromatographic column that minimizes the use of extra devices to trap and transfer the analytes in the sample to be measured.

It is a further object of the present invention to provide a system for interfacing a sampling device and a chromatograph and for pre-concentrating analytes in a sample prior to introducing the sample into the chromatographic column that eliminates the use of valves in the flow path of the analytes to be measured.

It is yet another object of the present invention to provide a system for interfacing a sampling device and a chromatograph and for pre-concentrating analytes in a sample prior to introducing the sample into the chromatographic column that where the sampling device, adsorbent trap, and chromatograph are in very close proximity to one another.

It is still another object of the present invention to provide a system for interfacing a sampling device and a chromatograph and for pre-concentrating analytes in a sample prior to introducing the sample into the chromatographic column that adsorbs analytes as fluid carrying the analytes flows in one direction and desorbs the analytes as fluid flows in the opposite direction.

To overcome the deficiencies of the prior art and to achieve at least some of the objects and advantages listed, the invention comprises an interface assembly for pre-concentrating analytes in chromatography, including an interface housing having a first end and a second end, wherein the first end is adapted to be coupled to a sampling device and the second end is adapted to be coupled to a chromatograph, and wherein the interface housing has a first flow channel, an adsorbent housing connected to the interface housing, the adsorbent housing having a second flow channel, an inlet, and an outlet, a first valveless conduit through which fluid is communicated between the sampling device and the first flow channel, a second valveless conduit through which fluid is communicated between the first flow channel and the second flow channel, a third valveless conduit through which fluid is communicated from the first flow channel to the chromatograph, and at least one adsorbent disposed in the second flow channel such that the adsorbent adsorbs analytes when fluid carrying the analytes flows through the second valveless conduit, through the second flow channel, and through the outlet, and the adsorbent desorbs the analytes when fluid flows through the inlet, through the second flow channel, and through the second valveless conduit.

DETAILED DESCRIPTION OF THE DRAWINGS

Figure 1:
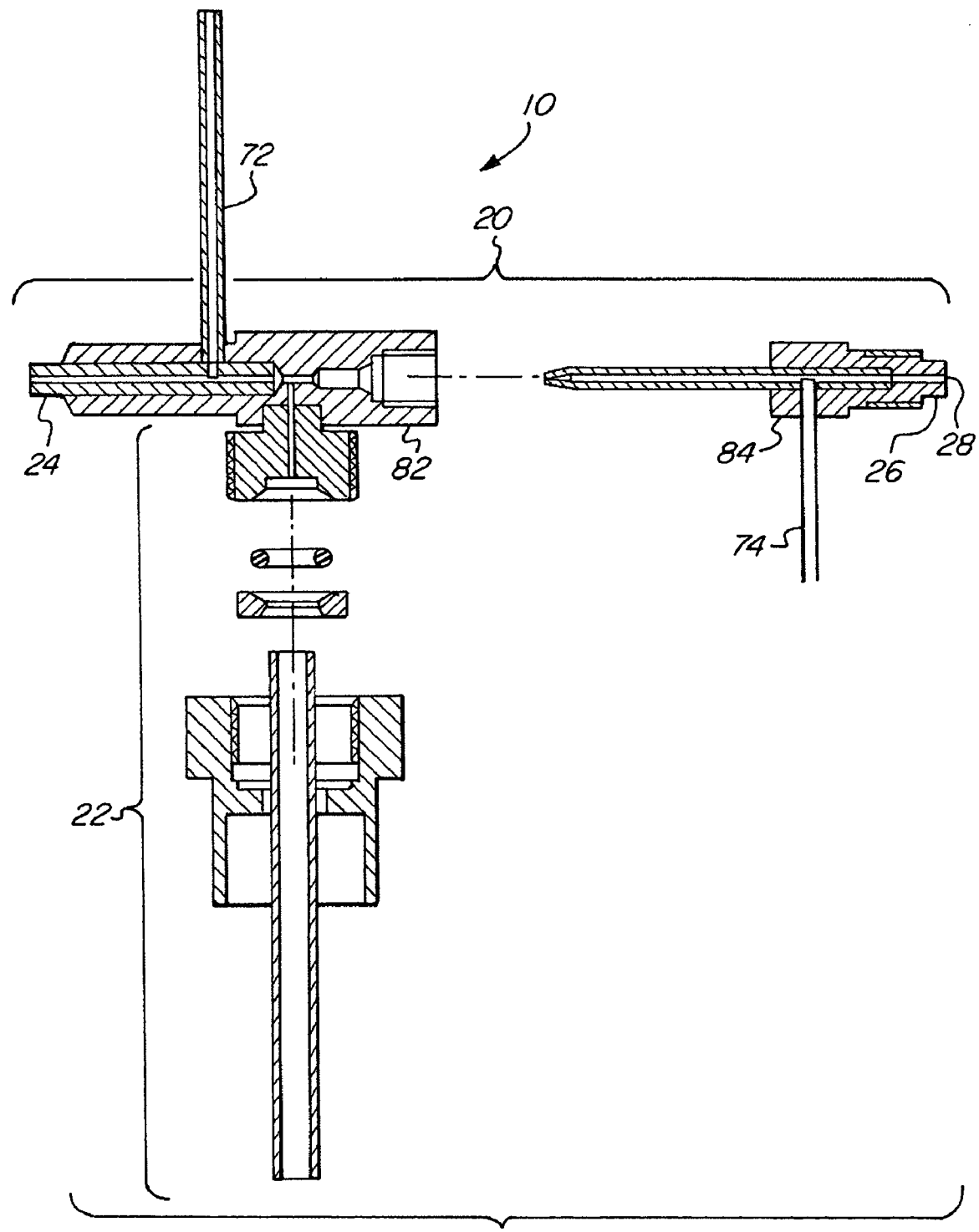
FIG. 1 is a cross-sectional, exploded view of an interface assembly for pre-concentrating analytes in accordance with invention.

The basic components of one embodiment of an interface assembly for pre-concentrating analytes 10 in accordance with the invention are illustrated in FIG. 1. As used in the description, the terms "top," "bottom," "above," "below," "over," "under," "on top," "underneath," "up," "down," "upper," "lower," "front," "rear," "forward" and "back" refer to the objects referenced when in the orientation illustrated in the drawings, which orientation is not necessary for achieving the objects of the invention.

Figure 6:
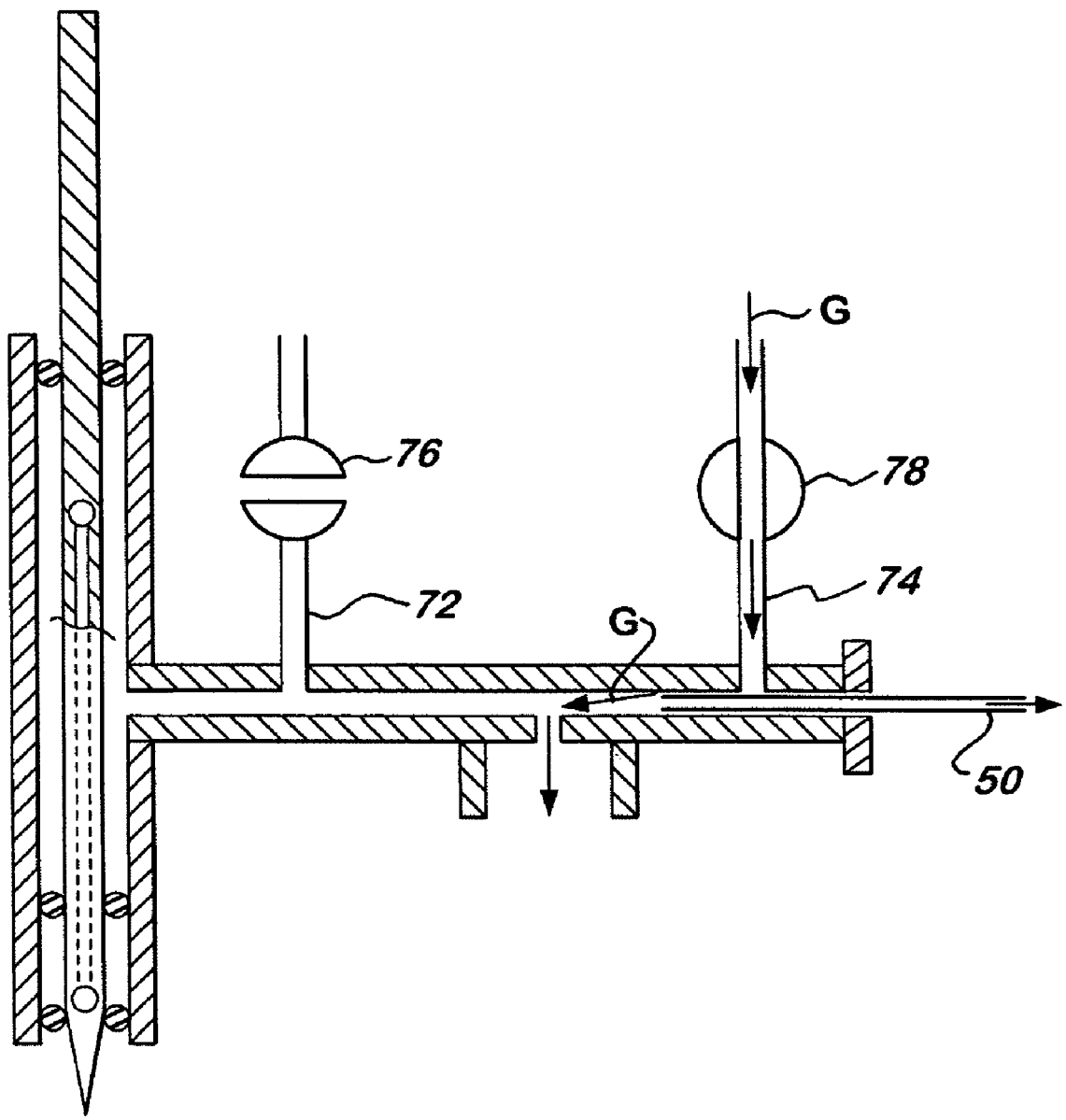
FIG. 6 is a schematic view of the interface assembly of FIG. 2 during the system maintenance stage.

The interface assembly 10 includes an interface housing 20 and an adsorbent housing 22 connected thereto. In certain advantageous embodiments, the interface housing 20 and the adsorbent housing 22 have corresponding threaded portions so that the adsorbent housing 22 can be easily connected to and removed from the system (as shown in FIG. 6). However, in other embodiments, the adsorbent housing 22 may be connected to the system via any other means providing an adequate seal such that fluid leakage does not occur, and in some cases, the adsorbent housing 22 is even integrally formed with the interface housing 20.

The interface housing 10 has a first end 24 and a second end 26. The first end 24 is adapted to be coupled to sampling device, such as, for example, a headspace sampler. The second end 26 is adapted to be coupled to a chromatograph. This may be accomplished, for example, by the use of a column port 28 in the interface housing 20 for receiving the end of a chromatographic column.

The sampling device to which the first end 24 of the interface housing 20 is coupled will typically include some vessel or area for holding and/or extracting a sample containing analytes to be measured. For example, referring to FIG. 2, the sampling device may include a sampling needle 30 and a sample chamber 32, where the sampling needle has a vessel port 34 through which fluid is communicated between the needle 30 and a vessel 38 and a sample chamber port 36 through which fluid is communicated between the needle 30 the sample chamber 32.

The interface housing 20 has a first flow channel 40 therein, and a first valveless conduit 42 permits fluid to be communicated between the sample chamber 32 and first flow channel 40. The adsorbent housing 22 has a second flow channel 44, and a second valveless conduit 46 permits fluid to be communicated between the first flow channel 40 and the second flow channel 44.

As noted above, in some embodiments, the interface housing 20 has a column port 28 for receiving the end of a chromatographic column 50. A third valveless conduit 48 permits fluid to be communicated between the first flow channel 40 and the column 50. The third valveless conduit 48 may comprise a channel of the column port 28 that is in fluid communication with the first flow channel 40 and is especially adapted for receiving the end of the column 50, or it may comprise a portion of the first flow channel 40 adjacent to the end of the column 50, or it may simply be the end of the column 50 itself.

At least one adsorbent 60 is disposed in the second flow channel 44 in order to adsorb the analytes in the sample as the sample fluid passes through the second valveless conduit 46 and down through the second flow channel 44. In certain advantageous embodiments, a weaker adsorbent 62 is positioned between the second valveless conduit 46 and the adsorbent 60. Accordingly, as the sample fluid passes through the second valveless conduit 46 and down through the second flow channel 44, the weaker adsorbent 62 first adsorbs the heavier compounds, and the stronger adsorbent 60 then adsorbs the more volatile compounds in the sample.

In some embodiments, the adsorbents 60, 62 are hydrophobic, thereby allowing moisture to be easily purged from the system by a carrier gas, as further explained below. In certain advantageous embodiments, graphitized carbon black is used as an adsorbent. In some embodiments, a polymeric adsorbent is used. In certain embodiments, a carbon molecular sieve is used.

In some embodiments, the adsorbent housing 22 is temperature controllable. Accordingly, the housing 22 can be heated to desorb analytes that have been retained by the adsorbents 60, 62 before a fluid sweeps them out of the housing 22 and into the column 50.

The adsorbent housing 22 has an inlet 64 and an outlet 66. In certain advantageous embodiments, the inlet 64 and outlet 66 both communicate with the second flow channel 44 via a common passage 68, and a single valve 70 switches between the inlet 64 and the outlet 66. However, in other embodiments, separate passages and valves are used to provide for the inlet and outlet of fluid to and from the second flow channel 44.

The interface housing 20 has a first inlet 72 for generally providing needed fluid to the system. For instance, the first inlet 72 may provide carrier gas to different parts of the system at different stages of operation, such as, for example, by providing the sampling device with fluid to pressurize the vessel 38, or, as another example, by providing carrier gas to the adsorbent housing 22 to carry a sample containing analytes thereto or to sweep away moisture contained therein. The interface housing 20 also has a second inlet 74 for providing fluid that may be used by various parts of the system at various stages, but primarily for isolating the chromatographic column 50 from the rest of the system in order to keep fluid from entering the column 50 until it is specifically desired to desorb the analytes thereinto. Valves 76, 78 are provided to open and close inlets 72, 74, respectively.

In some embodiments, the interface housing 22 has first and second portions 82, 84 (as shown in FIG. 1), which can be coupled together, where the first portion 82 includes the first inlet 72 and the second portion 84 includes the second inlet 74. It should be noted that, in these and other embodiments, the first flow channel 40 may be comprised of multiple subchannels in various interface housing portions (such as portions 82, 84), and of varying shapes and thicknesses, which, in conjunction, form a continuous channel.

Figure 2:
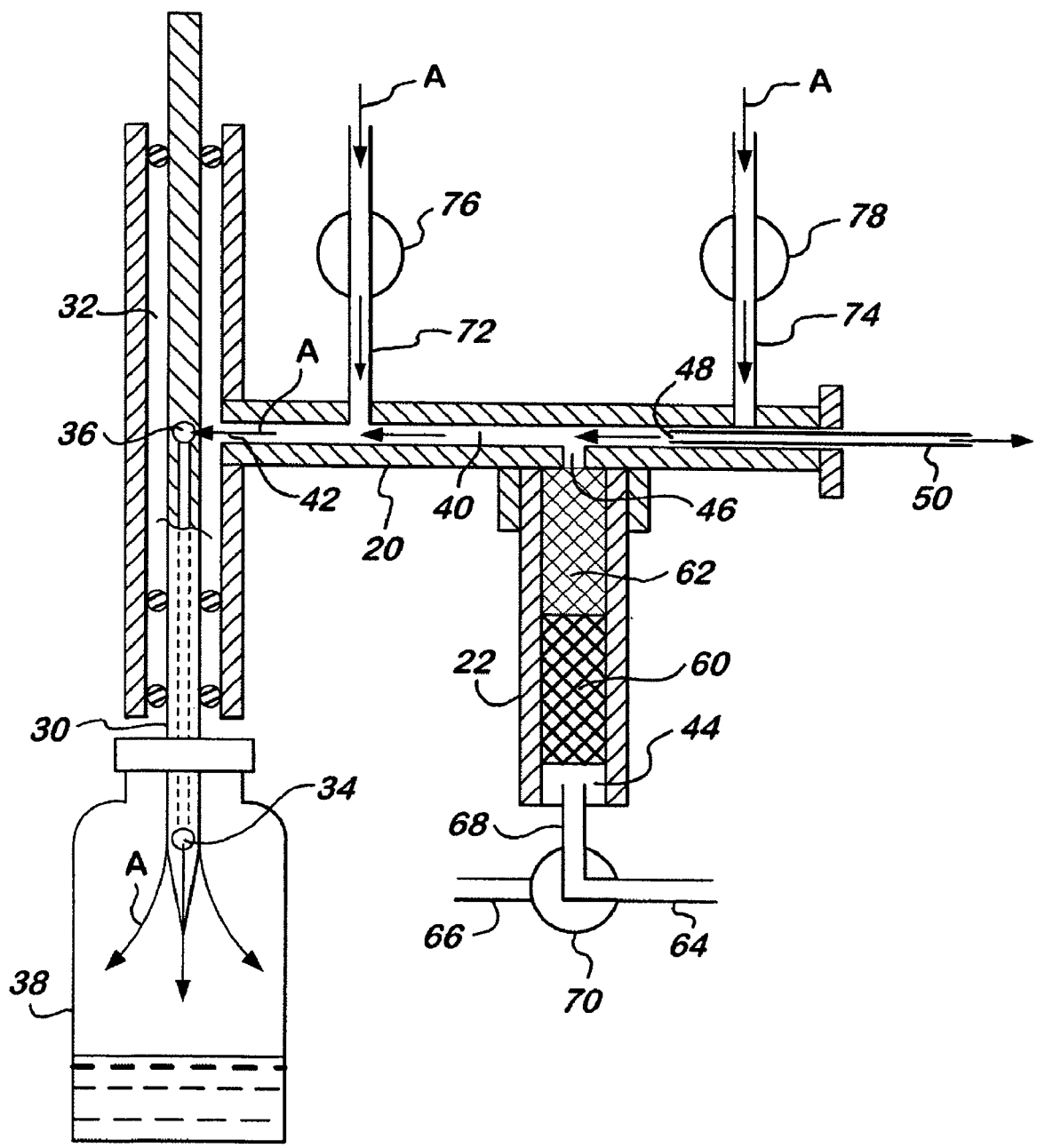
FIG. 2 is a schematic view of the interface assembly of FIG. 1 in use with a headspace sampler and a chromatographic column during the vessel pressurization stage.

Operation of the above described assembly is illustrated stepwise in FIGS. 2-6. A pressurization step is illustrated in FIG. 2. As shown therein, the sampling needle descends into the vessel 38, bringing the vessel port 34 into fluid communication with the interior of the vessel 38. The inlets 76, 78, and 64 are all open, sending fluid into the sample chamber 32, through the chamber port 36, down through the needle 30, and into the vessel 38 (indicated by arrows A). In this way, the vessel is pressurized.

Figure 3:
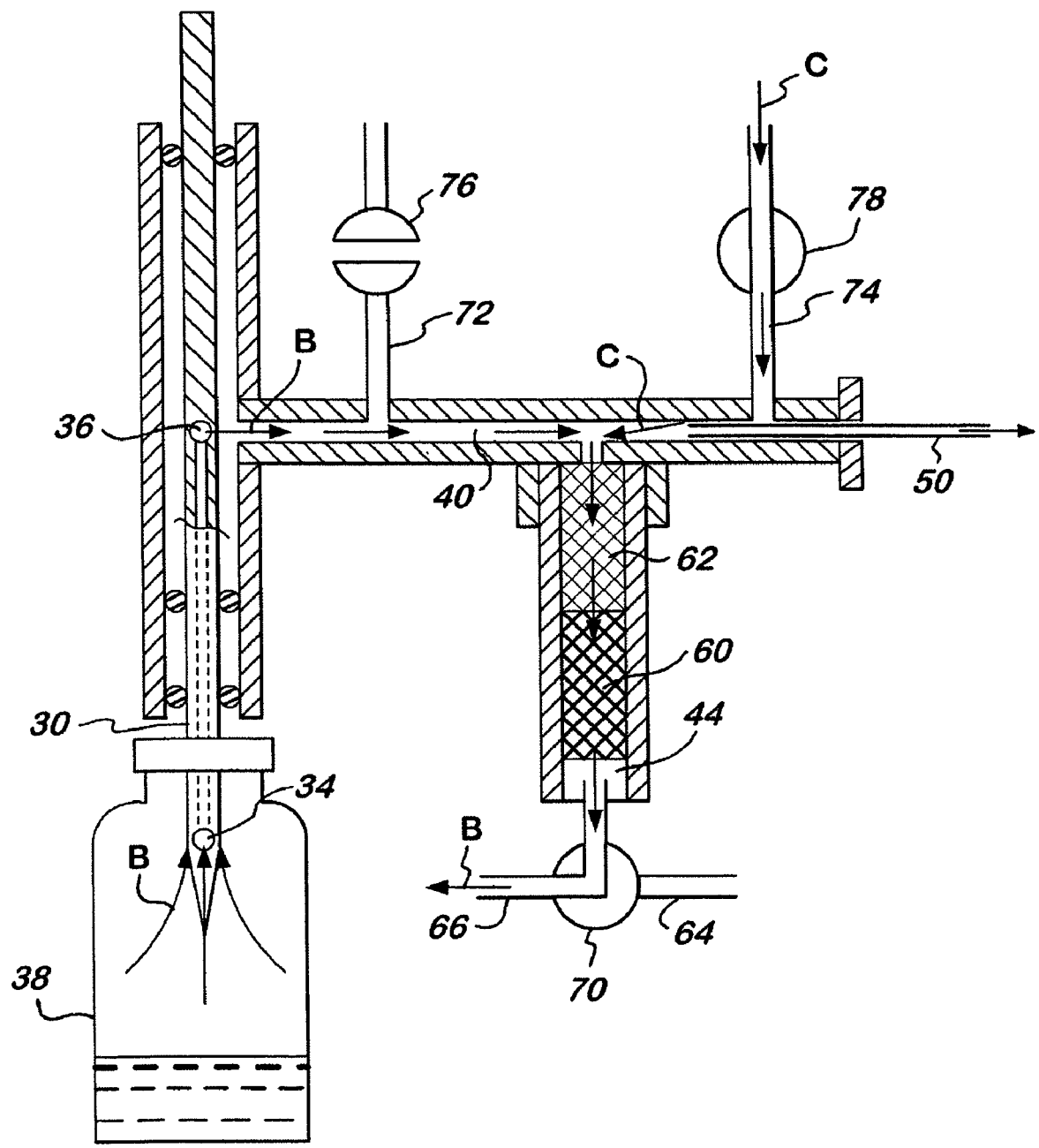
FIG. 3 is a schematic view of the interface assembly of FIG. 2 during the trap load stage.

A trap load step is illustrated in FIG. 3. As shown therein, the inlet valve 76 is closed, terminating the supply of fluid from the inlet 72. Likewise, the valve 70 terminates the supply of fluid from inlet 64, and opens the outlet 66. As a result, fluid containing the analytes to be measured elute from the vessel 38 through the vessel port 34, through the needle 30, out the chamber port 36, into the first flow channel 40, into the second flow channel 44 and through the adsorbents 62, 60, which adsorb the analytes before the fluid is discharged through the outlet 66 (indicated by arrows B). The inlet valve 78 remains open, allowing fluid to continue to enter through the inlet 74 and isolate the column 50 (indicated by arrows C).

Figure 4:
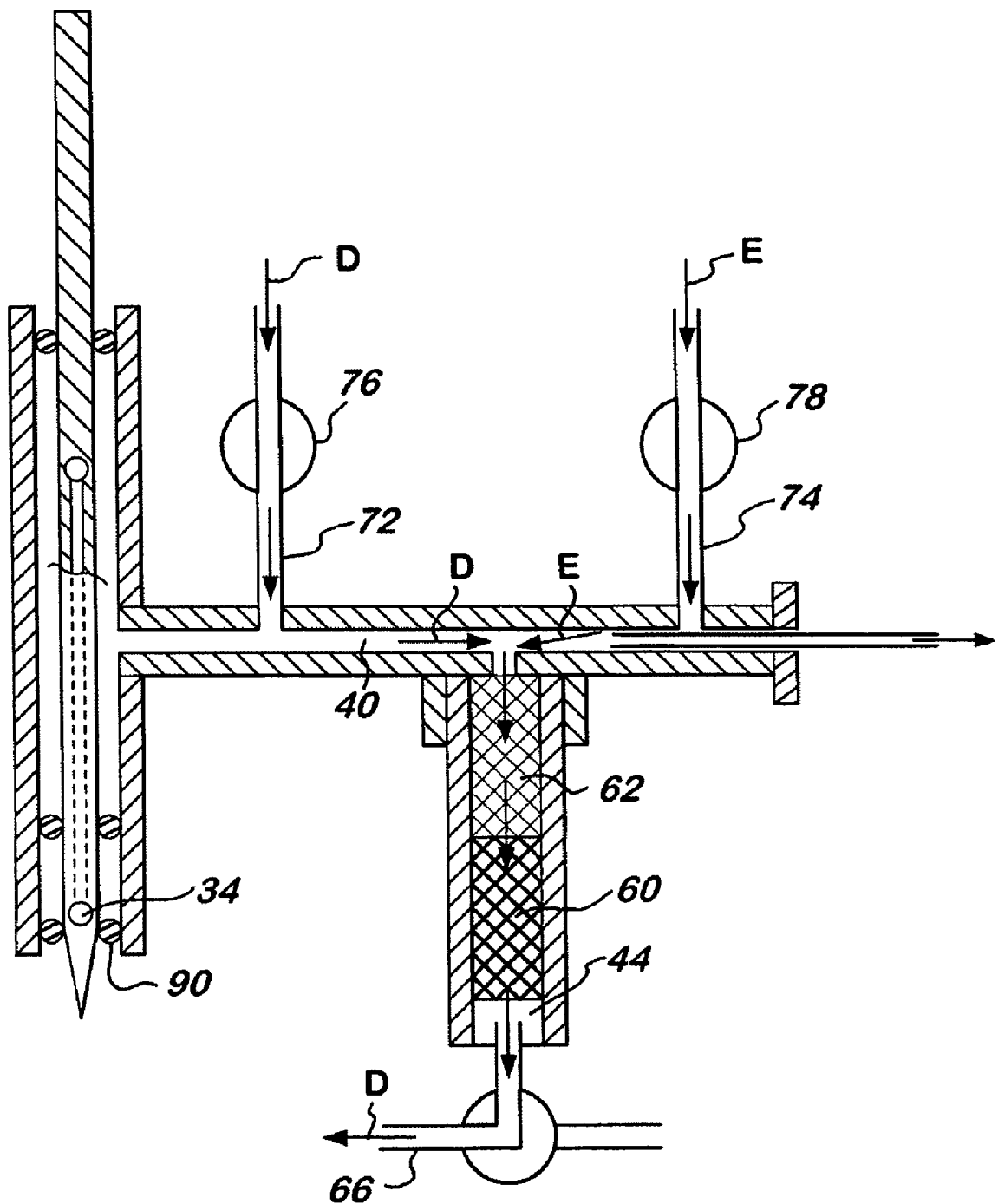
FIG. 4 is a schematic view of the interface assembly of FIG. 2 during the trap purge stage.

In embodiments where a significant amount of moisture is present in the sample being analyzed, a dry purge step may be desired, which is illustrated in FIG. 4. As shown, the needle 30 is withdrawn from the vessel 38, bringing the vessel port 34 above the seal 90. The inlet valve 76 is opened again, thereby allowing fluid to once again enter the system via the inlet 72. The fluid flows into the first flow channel 40, into the second flow channel 44 and through the adsorbents 62, 60, sweeping any moisture therein out through the outlet 66 (indicated by arrows D). Once again, the inlet valve 78 remains open, allowing fluid to continue to enter through the inlet 74 and isolate the column 50 (indicated by arrows E).

Figure 5:
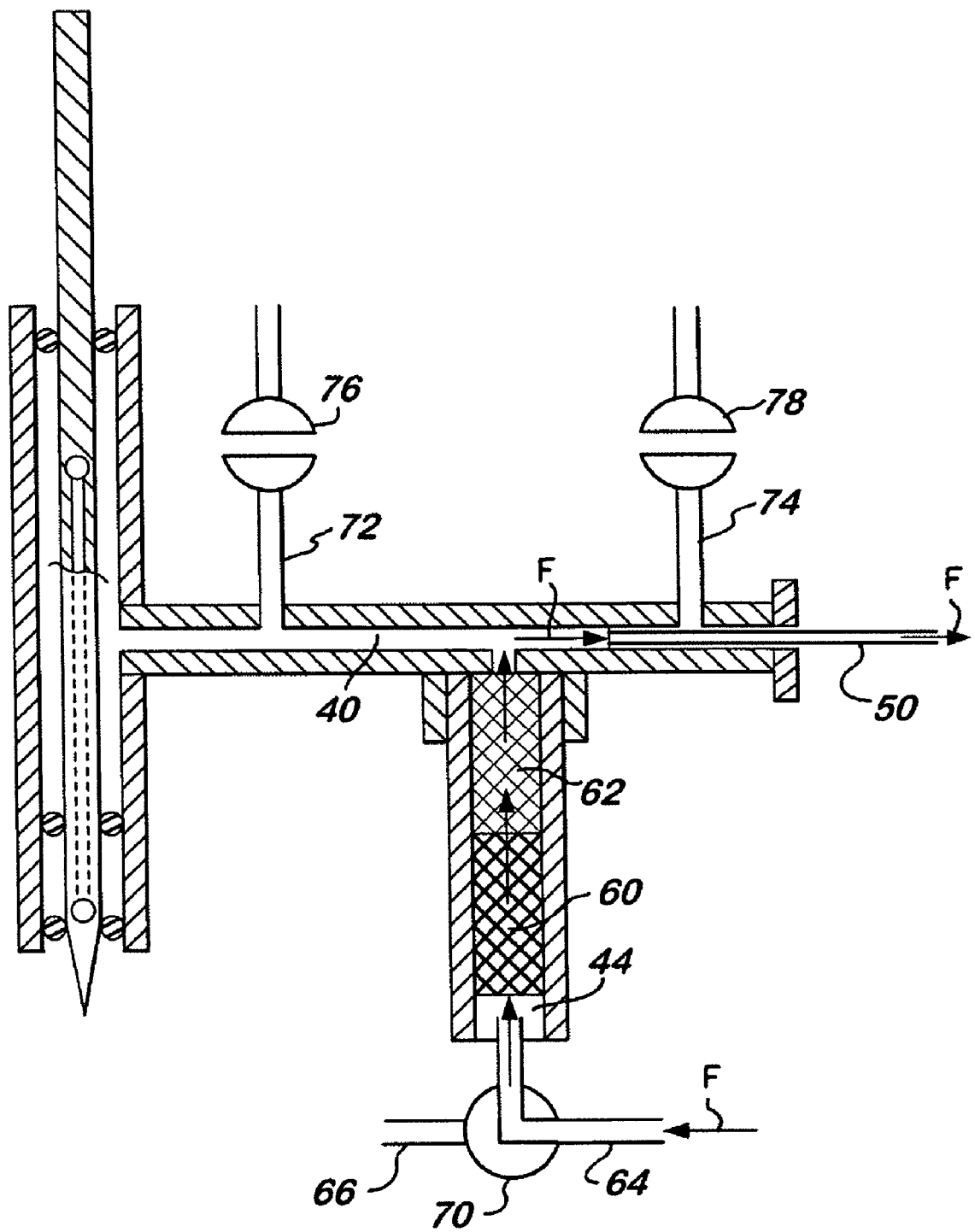
FIG. 5 is a schematic view of the interface assembly of FIG. 2 during the trap desorption stage.

A desorption step is illustrated in FIG. 5. As shown therein, the valves 76, 78 are closed, terminating the supply of fluid from inlets 72, 74. The valve 70 closes the outlet 66 and re-opens the inlet 64. The adsorbent housing 22 is heated to desorb the analytes retained by the adsorbents 62, 60. Fluid enters through the inlet 64, flows into the second flow chamber 44, sweeping the desorbed analytes into the first flow chamber 40 and into the chromatographic column 50 (indicated by arrows F).

FIG. 6 illustrates an arrangement for system maintenance when the sampling device or the adsorbent housing 22 is disconnected from the interface housing 20. As shown therein, the valve 76 remains closed. The inlet valve 78 remains open, allowing fluid to enter through the inlet 74 and flow past the inlet of the column 50 to prevent ambient air from entering the column (indicated by arrows G).

In certain advantageous embodiments, the first flow channel 40 will have a very small inner diameter in order to minimize the surface area over which the sample containing the analytes flows and to help prevent any flow resulting from dispersion that may otherwise flow back towards the sample chamber 32 during the trap desorption stage illustrated in FIG. 5. In some embodiments, this inner diameter is between 0.1 and 1.0 mm, and in certain advantageous embodiments, is about 0.5 mm.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. An interface assembly for pre-concentrating analytes in chromatography, comprising:
    a headspace sampler having at least one sample vessel and a sample chamber that receives a sample extracted from the vessel;
    an interface housing having a first end and a second end, wherein the first end is adapted to be coupled to said headspace sampler and the second end is adapted to be coupled to a chromatograph, and wherein said interface housing has a first flow channel;
    an adsorbent housing connected to said interface housing, said adsorbent housing having a second flow channel, an inlet in fluid communication with the second flow channel, and an outlet in fluid communication with the second flow channel;
    a first valveless conduit through which fluid is communicated between the sample chamber and the first flow channel;
    a second valveless conduit through which fluid is communicated between the first flow channel and the second flow channel;
    a third valveless conduit through which fluid is communicated from said first flow channel to the chromatograph; and
    at least one adsorbent disposed in said second flow channel such that said adsorbent adsorbs analytes when fluid carrying the analytes flows through the second valveless conduit, through the second flow channel, and through the outlet, and said adsorbent desorbs the analytes when fluid flows through the inlet, through the second flow channel, and through the second valveless conduit.

2. An interface assembly for pre-concentrating analytes as claimed in claim 1, further comprising a chromatographic column having an end disposed in the first flow channel, wherein said third valveless conduit comprises the end of the chromatographic column.

3. An interface assembly for pre-concentrating analytes as claimed in claim 1, wherein said interface housing includes first and second inlets in fluid communication with the first flow channel.

4. An interface assembly for pre-concentrating analytes as claimed in claim 3, wherein:
    said interface housing comprises a first portion and a second portion;
    said first portion includes the first inlet; and
    said second portion includes the second inlet.

5. An interface assembly for pre-concentrating analytes as claimed in claim 3, wherein said headspace sampler further includes a sampling needle with a vessel port in fluid communication with the vessel and a chamber port in fluid communication with the sample chamber, further comprising:
- a chromatographic column coupled to the second end of the interface housing; and
- a plurality of valves for opening and closing the first and second inlets of said interface housing, the inlet of the adsorbent housing, and the outlet of the adsorbent housing;

wherein:
- when the vessel port of the sampling needle is positioned in the vessel, the outlet of the adsorbent housing is closed, and the first and second inlets of the interface housing and the inlet of the adsorbent housing are open, fluid flows into the vessel and pressurizes the vessel;
- when the vessel port of the sampling needle is positioned in the vessel, the first inlet of the interface housing and the inlet of the adsorbent housing are closed, and the second inlet of the interface housing and the outlet of the adsorbent housing are open, fluid flows from the sampling device, into the first flow channel, into the second flow channel, where the adsorbent adsorbs the analytes in the fluid, and out through the outlet;
- when the vessel port of the sampling needle is positioned within the sample chamber, the inlet of the adsorbent housing is closed, and the first and second inlets of the interface housing and the outlet of the adsorbent housing are open, carrier gas flows into the first flow channel, into the second flow channel, where moisture is carried away by the carrier gas, and out through the outlet; and
- when the vessel port of the sampling needle is positioned within the sample chamber, the first and second inlets of the interface housing and the outlet of the adsorbent housing is closed, and the inlet of the adsorbent housing is open, fluid flows into the second flow channel, where the analytes are desorbed, into the first flow channel, and into the chromatographic column.

6. An interface assembly for pre-concentrating analytes as claimed in claim 1, further comprising:
- a passage through which fluid is communicated from the second flow channel to the outlet of the adsorbent housing, and through which fluid is communicated from the inlet of the adsorbent housing to the second flow channel; and
- a valve located in said passage for switching between the inlet and outlet of the adsorbent housing.

7. An interface assembly for pre-concentrating analytes as claimed in claim 1, wherein said interface housing and said adsorbent housing have corresponding threaded portions for connecting said adsorbent housing to said interface housing.

8. An interface assembly for pre-concentrating analytes as claimed in claim 1, wherein said adsorbent housing is integrally formed with said interface housing.

9. An interface assembly for pre-concentrating analytes as claimed in claim 1, wherein said adsorbent housing is temperature-controllable.

10. An interface assembly for pre-concentrating analytes as claimed in claim 1, wherein said at least one adsorbent is hydrophobic.

11. An interface assembly for pre-concentrating analytes as claimed in claim 10, wherein said at least one adsorbent comprises carbon black.

12. An interface assembly for pre-concentrating analytes as claimed in claim 10, wherein said at least one adsorbent comprises a polymeric adsorbent.

13. An interface assembly for pre-concentrating analytes as claimed in claim 10, wherein said at least one adsorbent comprises a carbon molecular sieve.

14. An interface assembly for pre-concentrating analytes as claimed in claim 1, wherein:
- said at least one adsorbent comprises first and second adsorbents;
- said second adsorbent is stronger than said first adsorbent; and
- said first adsorbent is disposed between said second valveless conduit and said second adsorbent.

15. An interface assembly for pre-concentrating analytes as claimed in claim 1, wherein the first flow channel has a diameter between 0.1 and 1.0 mm.

16. An interface assembly for pre-concentrating analytes as claimed in claim 13, wherein the first flow channel has a diameter of about 0.5 mm.

* * * * *